United States Patent [19]

Ukawa et al.

[11] Patent Number: 5,355,882
[45] Date of Patent: Oct. 18, 1994

[54] PULSE OXIMETER

[75] Inventors: Teiji Ukawa; Kazumasa Ito; Tadashi Nakayama, all of Tokyo, Japan

[73] Assignee: Nihon Kohden Corporation, Tokyo, Japan

[21] Appl. No.: 87,314

[22] Filed: Jul. 8, 1993

[30] Foreign Application Priority Data

Jul. 9, 1992 [JP] Japan .................. 4-181946

[51] Int. Cl.$^5$ .............................................. A61B 5/00
[52] U.S. Cl. .................................... 128/633; 356/41
[58] Field of Search ............... 128/633, 634, 637, 664, 128/665; 356/39-41

[56] References Cited

U.S. PATENT DOCUMENTS

| | | | |
|---|---|---|---|
| 4,641,658 | 2/1987 | Lepper | 356/39 X |
| 4,913,150 | 4/1990 | Cheung et al. | 128/633 |
| 5,054,916 | 10/1991 | Kanda et al. | 128/633 X |
| 5,127,406 | 7/1992 | Yamaguchi | 128/633 |
| 5,149,503 | 9/1992 | Kohno et al. | 356/41 X |
| 5,154,176 | 10/1992 | Kanda | 128/633 |
| 5,190,038 | 3/1993 | Polson et al. | 128/633 |
| 5,267,562 | 12/1993 | Ukawa et al. | 128/633 |

Primary Examiner—Lee S. Cohen
Assistant Examiner—Samuel Gilbert
Attorney, Agent, or Firm—Sughrue, Mion, Zinn, Macpeak & Seas

[57] ABSTRACT

A improved pulse oximeter comprises first and second light-emitting diodes that apply red light and infrared light, respectively, to a living tissue including the arterial blood, a photodiode for detecting optical outputs as produced after the red and infrared light of two wavelengths issuing from light-emitting diodes have been absorbed by the living tissue, a first computing unit that computes the ratio between the pulsating components of light absorbance $\Phi$ for the two wavelengths due to the arterial blood on the basis of the dc components and pulsating components of the respective wavelengths that are obtained from the reception outputs of the photodiode, a correction circuit that not only detects the degree of fluctuation in the absorbance ratio $\Phi$ as produced from the first computing unit but which also holds the pulsating components of the respective wavelengths when they are stable and which, if there is a fluctuation in the absorbance ratio $\Phi$, computes a corrected absorbance ratio $\Phi'$ using the pulsating components of the respective wavelengths that were held at the stable time and the dc components of the respective wavelengths at the present time, and a second computing unit 16 for computing the oxygen saturation of arterial blood on the basis of the absorbance ratio $\Phi'$ as produced from the correction circuit. This pulse oximeter permits the intended measurement to be continued consistently even if there occurs noise due to body movements and yet it is capable of measurements with good response.

2 Claims, 3 Drawing Sheets

PULSE OXIMETER

BACKGROUND OF THE INVENTION

1. Field of Industrial Utility

The present invention relates to a pulse oximeter with which the oxygen saturation of the arterial blood of a subject can be measured continuously in a non-invasive manner using the difference in absorption characteristics between red light and infrared light at two different wavelengths. More specifically, the present invention relates to a pulse oximeter that is adapted for effective rejection of the noise component due to body movements.

2. Prior Art

Pulse oximeters have conventionally been used to measure the oxygen saturation of arterial blood continuously in a bloodless manner. To use the pulse oximeter, the probe is attached to the tip of a subject's finger or the earlobe and both red and infrared light having different wavelengths are applied to the living body from the probe at given time intervals, and the oxygen saturation S is calculated from the ratio between the pulsating components of light absorbance, $\Phi$, as obtained from the transmitted or reflected light rays of different wavelengths. In a typical case, the red light has a reference wavelength of 660 nm and the infrared light has a wavelength of 940 nm; two light-emitting diodes for issuing these wavelengths and one photodiode for light reception are contained in the probe.

If the pulsating component of light absorbance at the wavelength of red light is written as $\Delta A1$ and the pulsating component of light absorbance for the wavelength of infrared light as $\Delta A2$, the absorbance ratio between the two different wavelengths $\Phi$ is given by:

$$\Phi = \Delta A1 / \Delta A2$$

The oxygen saturation S can be computed as a function f of this absorbance ratio $\Phi$:

$$S = f(\Phi)$$

The pulse oximeter operating by the principle described above has one serious problem; if the subject under pulse oximetry moves the finger to which the probe is attached, the volume of blood fluctuates and the measured value of absorbance ratio $\Phi$ fluctuates so greatly as to make it impossible to achieve the correct measurement of oxygen saturation S.

Under the circumstances, various attempts have heretofore been made to eliminate the effect of such noise due to body movements. For example, Unexamined Japanese Patent Application No. 160446/1974 teaches a pulse oximeter that performs processing with the limit of measurement specified in such a way that if noise occurs due to a body movement, entry of measurement data into an averaging routine is prohibited to insure that the noise will not be contained in the oxygen saturation to be computed. U.S. Pat. No. 4,407,290 describes a pulse oximeter that performs weighted averaging on measured values so that if the measured values fluctuate on account of body movements, less weighing is applied, thereby insuring that the oxygen saturation is computed without the effect of noise. PCT Patent Publication No. 500843/1987 teaches a pulse oximeter that performs measurements in synchronism with a cardiogram so that if noise occurs due to a body movement that is not pulsation, its entry as measurement data is prevented to insure that the oxygen saturation will not be computed erroneously.

The above-described prior art oximeters have their own problems. The first type which performs processing with the limit of measurement specified and the third type which performs processing in synchronism with a cardiogram have the problem that consistent measurements cannot be continued if there occurs noise due to body movements. The second type which performs averaging on measured values has the disadvantage of sacrificing the response characteristics.

SUMMARY OF THE INVENTION

The present invention has been accomplished in view of these problems of the prior art and has as an object providing a pulse oximeter that permits the intended measurement to be continued consistently even if there occurs noise due to body movements and which yet is capable of measurements with good response.

To attain this object, the present invention provides a pulse oximeter comprising:

a first and second light source that apply red light and infrared light, respectively, of two different wavelengths to a living tissue including the arterial blood;

a light-receiving element for detecting optical outputs as produced after the red and infrared light of two wavelengths emitted from said first and second light sources have been absorbed by the living tissue;

a first computing means that computes the ratio between the pulsating components of light absorbance for the two wavelengths due to the arterial blood on the basis of the dc components and pulsating components of the respective wavelengths that are obtained from the reception outputs of said light-receiving element;

a correction circuit that not only detects the degree of fluctuation in the absorbance ratio as produced from said first computing means but which also holds the pulsating components of said respective wavelengths when they are stable and which, if there is a fluctuation in the absorbance ratio, computes a corrected absorbance ratio using the pulsating components of the respective wavelengths that were held at the stable time and the dc components of the respective wavelengths at the present time; and a second computing means for computing the oxygen saturation of arterial blood on the basis of the absorbance ratio as produced from said correction circuit.

According to the present invention, the oximeter is such that if the absorbance ratio $\Phi$ is found to fluctuate on account of noise due to body movements, the values of the pulsating components of the reception outputs for two wavelengths at the stable time are held and the corrected absorbance ratio $\Phi'$ is determined from the held values and the latest values of the dc components of the reception outputs, and the oxygen saturation S is computed on the basis of that value of $\Phi'$. This is effective in minimizing the effect of noise due to body movements, thereby permitting the oxygen saturation S to be measured more correctly than in the prior art.

As a further advantage, the oximeter of the present invention which does not perform averaging on measured data enables the oxygen saturation to be measured with good response.

Even if noise occurs due to body movements, the measurement will not be interrupted as in the prior art and it can be continued as long as one desires, thereby offering the added advantage of permitting continuous monitoring of the oxygen saturation of the subject's arterial blood.

DETAILED DESCRIPTION OF THE PREFERRED EMBODIMENTS

The basic operational theory of the present invention is first described below.

Figure 1:
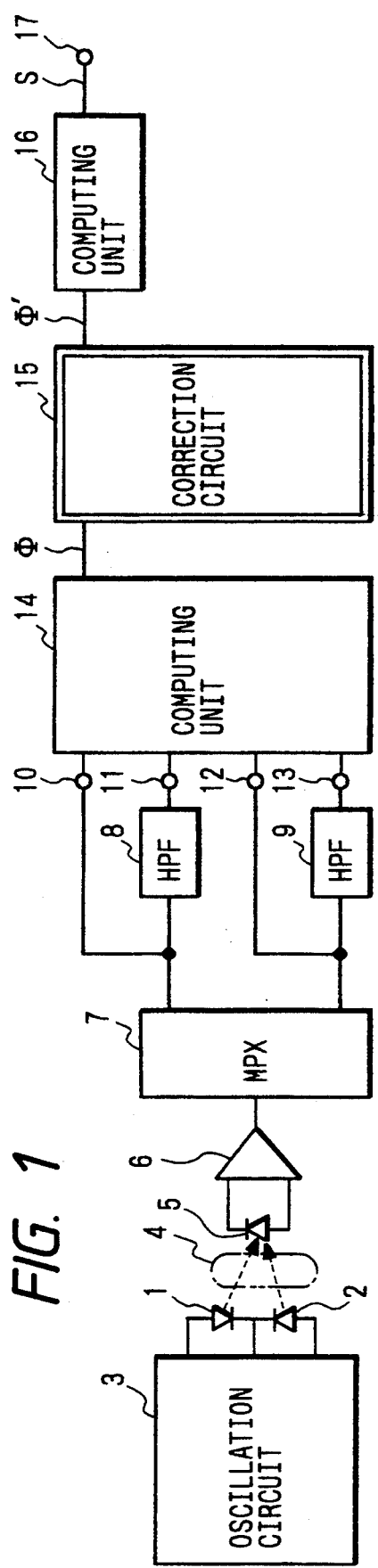
FIG. 1 is a block diagram showing a pulse oximeter according to an embodiment of the present invention.
Figure 4:
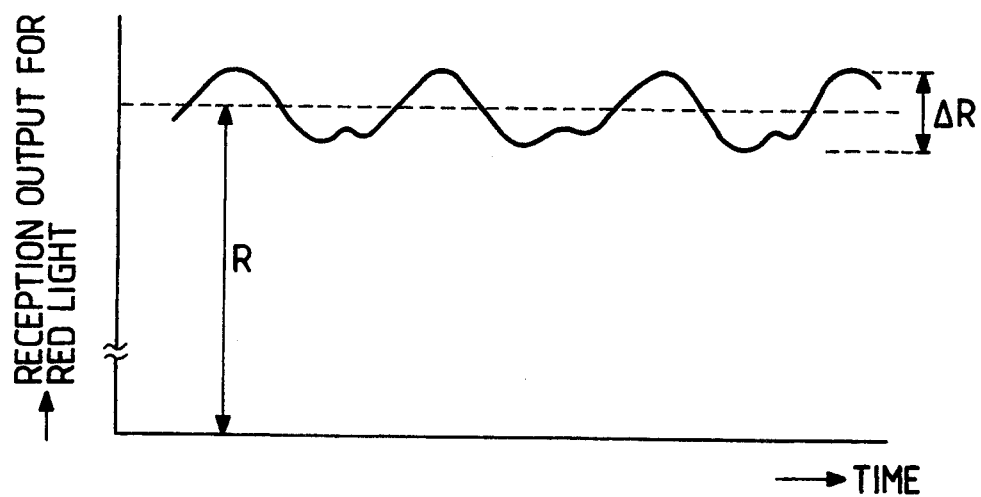
FIG. 4 is a waveform showing the waveforms of the dc and pulsating components of the reception output for red light.

Red light issuing from a first light-emitting diode 1 is launched into a living tissue 4 containing the arterial blood and the remainder of the light that is not absorbed by the tissue 4 is received by a photodiode 5 (see FIG. 1). If the dc component of the reception output of photodiode 5 is written as R and the pulsating component as $\Delta R$ (see FIG. 4), the pulsating component of light absorbance at the wavelength of the red light ($\Delta A1$) is given by:

$$\Delta A1 = \Delta R/R$$

Figure 5:
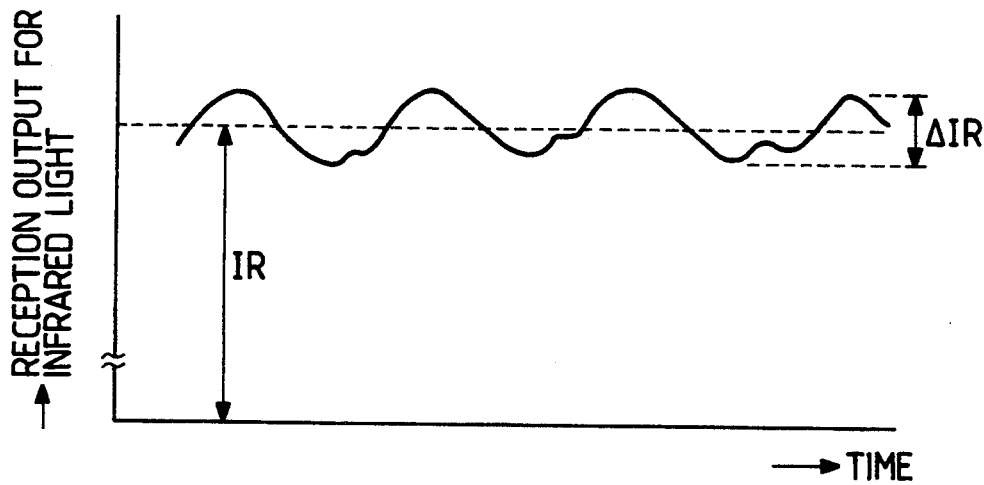
FIG. 5 is a waveform showing the waveforms of the dc and pulsating components of the reception output for infrared light.

On the other hand, infrared light issuing from a second light-emitting diode 2 is launched into the living tissue 4 and the remainder of the light that is absorbed by the tissue 4 is also received by the photodiode 5. If the dc component of the reception output of photodiode 5 is written as IR and the pulsating component as $\Delta IR$ (see FIG. 5), the pulsating component of light absorbance at the wavelength of the infrared light ($\Delta A2$) is given by:

$$\Delta A2 = \Delta IR/IR$$

Therefore, the ratio between the absorbance of two different wavelengths ($\Phi$) is:

$$\Phi = \Delta A1/\Delta A2$$
$$= (\Delta R/R)/(\Delta IR/IR)$$

which can be rewritten as:

$$\Phi = (\Delta R/\Delta IR) \times (IR/R)$$

In a typical case, the ratio of $\Delta R$ to R and that of $\Delta IR$ to IR are both 10% and below. It should also be mentioned that if the oxygen saturation S varies, both the dc and pulsating components will vary for each wavelength.

Suppose here that noise occurs due to a body movement, causing noise component N1 to be superposed on the reception output for red light whereas noise component N2 is superposed on the reception output for infrared light. In this case, the absorbance ratio $\Phi$ can be written as follows:

$$\Phi = \{(\Delta R + N1)/(\Delta IR + N2)\} \times \{(IR + N2)/(R + N1)\}.$$

where the dc components R and IR assume larger values than the respective pulsating components $\Delta R$ and $\Delta IR$ and, hence, are less subject to the effect of noise.

Therefore, in the present invention, the value of ($\Delta R/\Delta IR$) which is greatly influenced by noise is held at the time when it is stable and if the absorbance ratio $\Phi$ fluctuates due to noise, the held value of ($\Delta R/\Delta IR$) which may be denoted by ($\Delta R/\Delta IR$ (HOLD)) is used to compute $\Phi$. In this way, the oxygen saturation S that involves less effects of noise due to body movements can be measured continuously.

In the next place, we describe the technique of evaluating the degree of fluctuation in the absorbance ratio $\Phi$, as well as the technique of correcting $\Phi$ on the basis of the evaluated degree of fluctuation.

First, suppose that $\Phi$ is measured once per pulse. If $\Phi$ for the nth pulsation is written as $\Phi(n)$, $\Delta\Phi(n)$ or the first-order difference of $\Phi$ is given by:

$$\Delta\Phi(n) = \Phi(n) - \Phi(n-1)$$

Similarly, the second-order difference $\Delta^2\Phi(n)$ is given by:

$$\Delta^2\Phi(n) = \Delta(n) - \Delta\Phi(n-1)$$

The magnitude of this second-order difference $\Delta^2\Phi(n)$ is used to evaluate the fluctuation of $\Phi$. The coefficient k for representing the degree of fluctuation is expressed by:

$$k(n) = a \cdot \{\Delta^2\Phi(n) + \Delta^2\Phi(n+1) + \Delta^2\Phi(n+2)\}$$

where a is an appropriate constant. If k is greater than 1, the relation k=1 is used.

If the measured values of R and IR for the nth pulsation are written as R(n) and IR(n), respectively, $\Phi$(HOLD) which is the value of $\Phi$ computed using ($\Delta R/\Delta IR$ (HOLD))', or the corrected value of the held ($\Delta R/\Delta IR$ (HOLD)), is:

$$\Phi(\text{HOLD}) = (\Delta R/\Delta IR \text{ (HOLD)})' \times (IR(n)/R(n))$$

where ($\Delta R/\Delta IR$ (HOLD))' is given by:

$$(\Delta R/\Delta IR \text{ (HOLD)})' = (1-k')\{(\Delta R(n)\} + k'(\Delta R/\Delta IR \text{ (HOLD)})$$

where $\Delta R(n)$ and $\Delta IR(n)$ are the measured values of $\Delta R$ and $\Delta IR$ for the nth pulsation. The coefficient k' is expressed by:

$$k'(n) = b \cdot \{\Delta^2\Phi(n) + \Delta^2\Phi(n+1) + \Delta^2\Phi(n+2)\}$$

where b is another appropriated constant. If k' is greater than 1, the relation k'=1 is used.

Hence, the value of corrected $\Phi'$ can be determined by the following equation using k (the coefficient expressing the degree of fluctuation), $\Phi(n)$ (the measured value of $\Phi$ for the nth pulsation) and the value of $\Phi$(HOLD):

$$\Phi' = (1-k)\Phi(n) + k\Phi(\text{HOLD})$$

Using this corrected value $\Phi'$, the oxygen saturation S is computed by the following equation:

$$S = f(\Phi')$$

Thus, in the present invention, $\Phi$ is corrected to $\Phi'$ by incorporating $\Phi(\text{HOLD})$ in accordance with the value of coefficient k ($0 \leq k \leq 1$) representing the fluctuation of $\Phi$ and the oxygen saturation S involving less effects of noise can be determined on the basis of this corrected value $\Phi'$.

A pulse oximeter according to a specific embodiment of the present invention is described below in detail with reference to accompanying drawings.

FIG. 1 is a block diagram showing the pulse oximeter. Light-emitting diodes 1 and 2 are the first and second light sources in the oximeter of the present invention. They are driven alternately in response to pulse signals supplied from an oscillation circuit 3. Red light issuing from the first LED 1 is launched into the subject's living tissue 4 including the arterial blood and the remainder of the light that is absorbed by the tissue 4 is received by a photodiode 5 which serves as the light-receiving element in the oximeter. On the other hand, infrared light issues from the second LED 2 and is launched into the living tissue 4; the remainder of the light that is absorbed by the tissue 4 is also received by the photodiode 5.

The reception output of the photodiode 5 is amplified by an amplifier 6 and sent to a multiplexer (MPX) 7, where it is distributed in synchronism with the output from the oscillation circuit 3. The dc component R of the reception output for red light R is supplied into a computing unit 14 at an input terminal 10 whereas the pulsating component $\Delta R$ passed through a high-pass filter (HPF) 8 is supplied at another input terminal 11. On the other hand, the dc component IR of the reception output for infrared light IR is supplied into the computing unit 14 at a third input terminal 12 whereas the pulsating component $\Delta IR$ passed through a high-pass filter 9 is supplied at a fourth input terminal 13.

Computing unit 14 determines the absorbance ratio $\Phi$ using the following formula:

$$\Phi = (\Delta R/\Delta IR) \times (IR/R)$$

Figure 2:
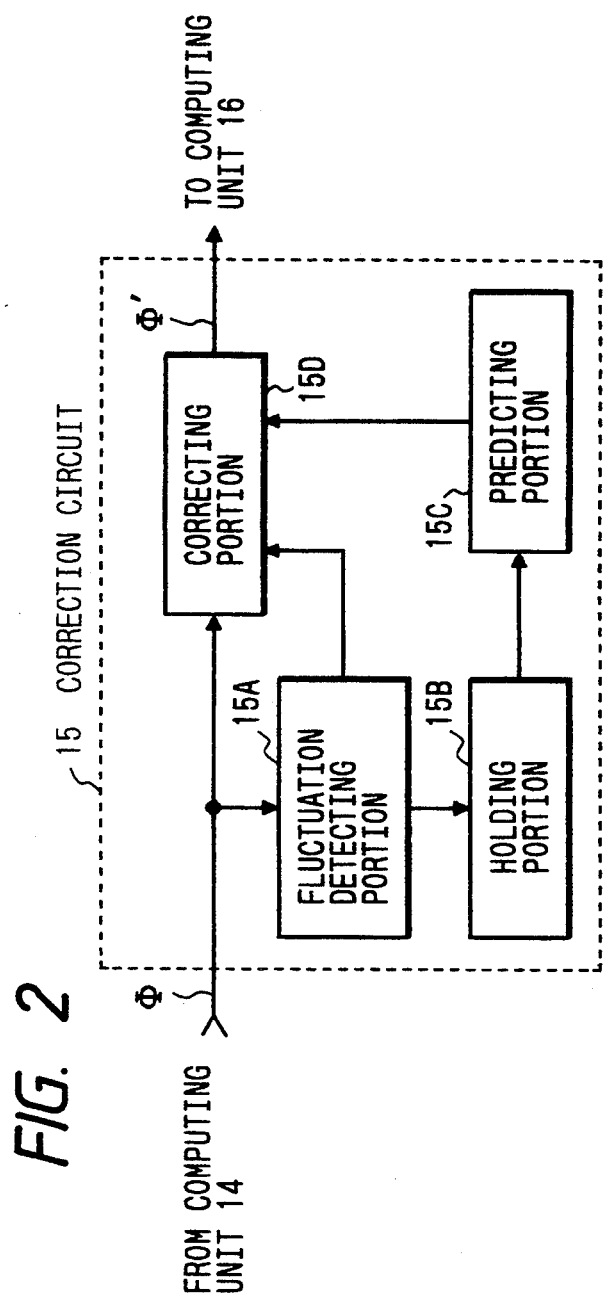
FIG. 2 is a block diagram showing the internal configuration of the correction circuit in the pulse oximeter of FIG. 1.

The computed value of $\Phi$ is entered into a correction circuit 15 at the next stage, which is shown in FIG. 2 more specifically.

Fluctuation detecting portion 15A which is part of the correction circuit 15 processes the input value of $\Phi$ to compute k(n) and k'(n) as follows:

$$k(n) = a \cdot \{\Delta^2 \Phi(n) + \Delta^2 \Phi(n+1) + \Delta^2 \Phi(n+2)\}$$

$$k'(n) = b \cdot \{\Delta^2 \Phi(n) + \Delta^2 \Phi(n+1) + \Delta^2 \Phi(n+2)\}$$

Thus, coefficients k and k' for evaluating the degree of fluctuation of $\Phi$ are determined.

The correction circuit 15 also includes a holding portion 15B. If, judging from the coefficients expressing the fluctuation of $\Phi$ that have been obtained in detecting portion 15A, $\Phi$ is found to fluctuate on account of noise due to body movements, holding portion 15B computes the corrected value $(\Delta R/\Delta IR \text{ (HOLD)})'$ from the values of $(\Delta R/\Delta IR \text{ (HOLD)})$ at the stable time and k' and holds the computed value.

Correction circuit 15 also includes a predicting portion 15C, in which $\Phi$ is predicted from both the latest value of $(IR(n)/R(n))$ being sent from the computing unit 14 and the value of $(\Delta R/\Delta IR(\text{HOLD}))'$ entered from the holding portion 15B and the thus predicted value of $\Phi$ is held as $\Phi(\text{HOLD})$. The prediction is accomplished by the following calculation:

$$\Phi(\text{HOLD}) = (\Delta R/\Delta IR \text{ (HOLD)})' \times (IR(n)/R(n))$$

A correcting portion 15D is the final part of correction circuit 15, in which the corrected value $\Phi'$ is computed by the following formula from the value of $\Phi$ being sent from the computing unit 14, the value of $\Phi(\text{HOLD})$ entered from the predicting portion 15C and the value of k supplied from the fluctuation detecting portion 15A:

$$\Phi' = (1-k)\Phi(n) + k\Phi(\text{HOLD})$$

The oximeter under discussion includes another computing unit 16 in the last stage and it computes the oxygen saturation S by the following formula based on the corrected value $\Phi'$ as supplied from the correction circuit 15:

$$S = f(\Phi')$$

The value of oxygen saturation S being delivered from output terminal 17 is displayed on a suitable device such as a monitor.

Figure 3:
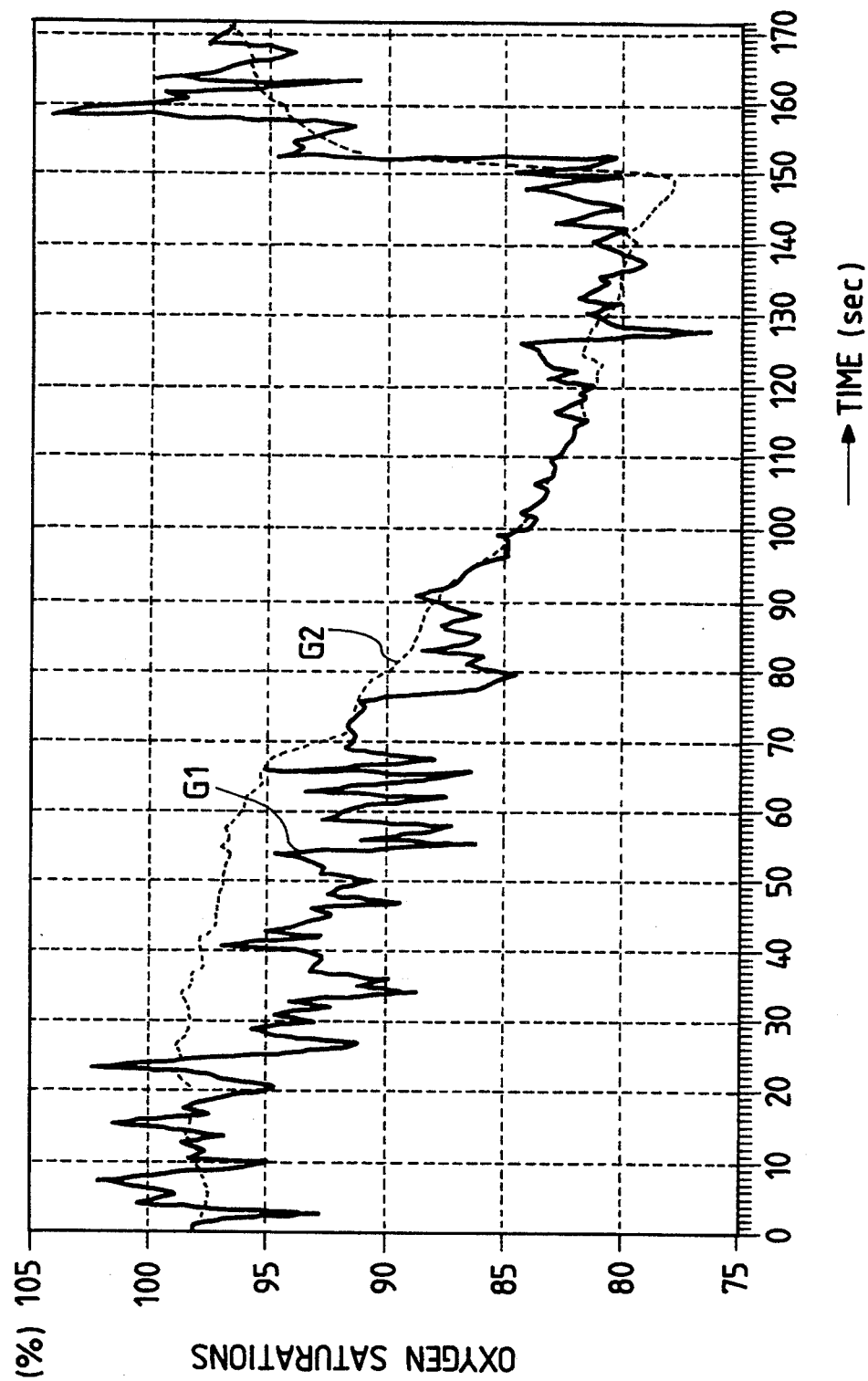
FIG. 3 is a graph in which the result of measurement of oxygen saturation S after correction is compared with the result of measurement of S before correction.

FIG. 3 is a chart showing the results of a measurement as conducted for the oxygen saturating S with the probe attached to the tip of a finger of a subject who moved the finger to produce noise. G1 in FIG. 3 refers to the curve of oxygen saturation S before correction and G2 refers to the curve of oxygen saturation S after correction. As is clear from FIG. 3, even if the value of absorbance ratio $\Phi$ fluctuates on account of noise due to body movements, it can be corrected in the correcting circuit 15 to provide the correct value of oxygen saturation S which involves less effects of the noise.

Thus, the technique of the present invention insures that even if the value of absorbance ratio $\Phi$ fluctuates, the measurement of oxygen saturation can be continued using the dc components of reception outputs; therefore, if the true value of oxygen saturation S changes, the result of measurement can be brought into compliance with that change in the same direction.

On the other hand, if the absorbance ratio $\Phi$ is stable, the mechanism of correction is hardly in action and, hence, the response characteristics of the oximeter will in no way be impaired.

As described on the foregoing pages, the oximeter of the present invention is such that if the absorbance ratio $\Phi$ is found to fluctuate on account of noise due to body movements, the values of the pulsating components of the reception outputs for two wavelengths at the stable time are held and the corrected absorbance ratio $\Phi'$ is determined from the held values and the latest values of the dc components of the reception outputs, and the oxygen saturation S is computed on the basis of that value of $\Phi'$. This is effective in minimizing the effect of noise due to body movements, thereby permitting the oxygen saturation S to be measured more correctly than in the prior art.

As a further advantage, the oximeter of the present invention which does not perform averaging on measured data enables the oxygen saturation to be measured with good response.

Even if the noise occurs due to body movements, the measurement will not be interrupted as in the prior art and it can be continued as long as one desires, thereby offering the added advantage of permitting continuous monitoring of the oxygen saturation of the subject's arterial blood.

What is claimed is:

1. A pulse oximeter comprising:
   a red light source and an infrared light source which apply red light and infrared light, respectively, having two different wavelengths to a living tissue including arterial blood;
   a light-receiving element which detects optical reception outputs after the red light and the infrared light having the two different wavelengths and which are respectively emitted from said red light source and said infrared light source haven been absorbed by the living tissue;
   first computing means for computing an absorbance ratio between pulsating components of light absorbance for the two different wavelengths due to the arterial blood, based on dc components and pulsating components of the respective two different wavelengths which are obtained from the reception outputs of said light-receiving element;
   correction circuit means for detecting a degree of fluctuation in the absorbance ratio outputted from said first computing means, for holding the pulsating components of said respective two different wavelengths when the pulsating components of said respective two different wavelengths are stable, and for computing a corrected absorbance ratio using the stable pulsating components of the respective two different wavelengths which were held and the dc components of the respective two different wavelengths at a present time when a fluctuation in the absorbance ratio exceeds a predetermined value; and
   a second computing means for computing an oxygen saturation of the arterial blood based on the absorbance ratio produced from said correction circuit means.

2. A pulse oximeter as claimed in claim 1, wherein said correction circuit means includes:
   a fluctuation detecting circuit means for computing a coefficient for evaluating a degree of fluctuation of the absorbance ratio based on the absorbance ratio transmitted from the first computing means;
   a holding circuit means for computing and holding the corrected absorbance ratio between the pulsating components of the red light and the infrared light in accordance with the coefficient and the absorbance ratio between the pulsating components of the red light and the infrared light in a stable condition when the fluctuation in the absorbance ratio exceeds said predetermined value;
   a predicting circuit means for predicting a held absorbance ratio in accordance with said corrected absorbance ratio transmitted from the holding circuit means and said absorbance ratio sent from the first computing means; and
   a correcting circuit means for computing said corrected absorbance ratio in accordance with the absorbance ratio sent from the first computing means, said held absorbance ratio transmitted from the predicting circuit means and the coefficient supplied from the fluctuation detecting circuit means.

* * * * *